United States Patent [19]

Muller et al.

[11] Patent Number: 5,728,844

[45] Date of Patent: Mar. 17, 1998

[54] IMMUNOTHERAPEUTIC AGENTS

[75] Inventors: George W. Muller, Bridgewater; Mary Shire, North Plainfield, both of N.J.

[73] Assignee: Celgene Corporation, Warren, N.J.

[21] Appl. No.: 578,738

[22] Filed: Dec. 26, 1995

Related U.S. Application Data

[63] Continuation-in-part of Ser. No. 520,710, Aug. 29, 1995.

[51] Int. Cl.$^6$ .............. C07D 209/48; C07D 209/46; C07D 217/24; A61K 31/40
[52] U.S. Cl. .............. 548/472; 548/477; 548/479; 546/142; 514/417; 514/416; 514/309
[58] Field of Search ............. 548/477, 479, 548/472; 546/142

[56] References Cited

U.S. PATENT DOCUMENTS 5,512,682  4/1996  Hilpest .................. 548/477

OTHER PUBLICATIONS

David Cavalla, et al., "Phosphodiesterase IV Inhibitors: Structural Diversity and Therapeutic Potential In Asthma", *Current Medical Chemistry*, 1995, 2, pp. 561–572.

Louis J. Lombardo, "Phosphodiesterase–IV Inhibitors: Novel Therapeutics for the Treatment of Inflammatory Diseases", *Current Pharmaceutical Design*, 1995, pp. 255–268.

John A. Lowe, III, et al., "The PDE IV family of calcium–independent phosphodiesterase enzymes", *Drugs of the Future*, 1992, 17(9):799–807.

Malcolm N. Palfreyman, "Phosphodiesterase type IV inhibitors as antiinflammatory agents", *Drugs of the Future*, 1995, 20(8):793–804.

Les Sekut, et al., "Pathophysiology and Regulation of TNF–α in Inflammation", *DN&P*,9(5), Jun. 1996, pp. 261–269.

*Primary Examiner*—Mukund J. Shah
*Assistant Examiner*—King Lit Wong
*Attorney, Agent, or Firm*—Mathews, Collins, Shepherd & Gould

[57] ABSTRACT

Novel amides are inhibitors of TNFα and phosphodiesterase and can be used to combat cachexia, endotoxic shock, retrovirus replication, asthma, and inflammatory conditions. A typical embodiment is 3-phthalimido-3-(3-cyclopentyloxy-4-methoxyphenyl)propionamide.

4 Claims, No Drawings

IMMUNOTHERAPEUTIC AGENTS

CROSS REFERENCE

This is a continuation-in-part of Ser. No. 08/520,710 filed Aug. 29, 1995.

DETAILED DESCRIPTION

The present invention pertains to a class of compounds which inhibit the action of phosphodiesterases, particularly PDE III and PDE IV, and the formation of tumor necrosis factor α, or TNFα, and the nuclear factor κB, or NFκB. These compounds can be diagrammatically represented by the formula:

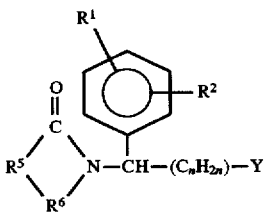

in which:
one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl, bicycloalkyl, or benzocycloalkyl of up to 18 carbon atoms;

X is a carbon-carbon bond, —$CH_2$—, or —O—;

$R^5$ is: (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, or lower alkoxy; (ii) the vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4–10 carbon atoms, unsubstituted or substituted with 1 to 3 substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, or phenyl; (iv) vinylene di-substituted with lower alkyl; or (v) ethylene, unsubstituted or mono-substituted or disubstituted with lower alkyl;

$R^6$ is —CO—, —$CH_2$—, or —$CH_2CO$—;

Y is —COZ, —C≡N, —$OR^8$, lower alkyl, or aryl;

Z is —$NH_2$, —OH, —NHR, —$R^9$, or —$OR^9$;

$R^8$ is hydrogen or lower alkyl;

$R^9$ is lower alkyl or benzyl; and, n has a value of 0, 1, 2, or 3.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neo-pentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The term cycloalkyl as used herein denotes a univalent saturated cyclic hydrocarbon chain. Unless otherwise stated, such chains can contain up to 18 carbon atoms. Monocycloalkyl refers to groups having a single ring. Polycycloalkyl denotes hydrocarbon groups having two or more ring systems having two or more ring atoms in common. Benzocycloalkyl denotes a monocyclic or polycyclic group fused to a benzo ring.

Representative of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Representative of polycycloalkyl groups are bicyclo[2.2.1]heptyl, bicyclo[3.2.1]octyl, and bicyclo[2.2.2]octyl. Benzocycloalkyl is typified by tetrahydronaphthyl, indanyl, and benzocycloheptanyl.

This invention also relates to a method of reducing the level of cytokines and their precursors in mammals and to compositions useful therein.

TNFα is a cytokine which is released primarily by mononuclear phagocytes in response to immunostimulators. When administered to animals or humans, TNFα can cause inflammation, fever, cardiovascular effects, hemorrhage, coagulation, and acute phase responses similar to those seen during acute infections and shock states.

NFκB is a pleiotropic transcriptional activator (Lenardo, et al., *Cell* 1989, 58, 227–29) which has been implicated in a variety of disease and inflammatory states. NFκB is thought to regulate cytokine levels including, but not limited to, TNFα and to be an activator of HIV transcription (Dbaibo et al., *J. Biol. Chem.* 1993, 17762–66; Dub et al., *Proc. Natl. Acad. Sci.* 1989, 86, 5974–78; Bachelerie et al., *Nature* 1991, 350, 709–12; Boswas et al., *J. Acquired Immune Deficiency Syndrome* 1993, 6, 778–786; Suzuki et al., *Biochem. and Biophys. Res. Comm.* 1993, 193, 277–83; Suzuki et al., *Biochem. and Biophys. Res. Comm.* 1992, 189, 1709–15; Suzuki et al., *Biochem. Mol. Bio. Int.* 1993, 31(4), 693–700; Shakhov et al., 1990, 171, 35–47; and Staal et al., *Proc. Natl. Acad. Sci. USA* 1990, 87, 9943–47. Thus inhibition of NFκB binding can regulate transcription of cytokine gene(s) and through this modulation and other mechanisms is useful in the inhibition of a multitude of disease states. TNFα and NFκB levels are influenced by a reciprocal feedback loop.

Many cellular functions which contribute to inflammatory conditions and diseases including asthma, inflammation, and other conditions are mediated by levels of adenosine 3',5'-cyclic monophosphate (cAMP). See, e.g., Lowe and Cheng, *Drugs of the Future*, 17(9), 799–807, 1992. It has been shown that the elevation of cAMP in inflammatory leukocytes inhibits their activation and the subsequent release of inflammatory mediators. Increased levels of cAMP also leads to the relaxation of airway smooth muscle. The primary cellular mechanism for the inactivation of cAMP is the breakdown of cAMP by a family of isoenzymes referred to as cyclic nucleotide phosphodiesterases (PDE), of which seven are known. It is recognized, for example, that the inhibition of PDE type IV is particularly effective in both the inhibition of inflammatory mediator release and the relaxation of airway smooth muscle. Thus, compounds which inhibit PDE IV specifically inhibit inflammation and relax airway smooth muscle, with a minimum of unwanted side effects such as cardiovascular or anti-platelet effects. It is now known that inhibition of TNFα production is a consequence of inhibition of PDE IV. Excessive or unregulated TNFα production has been implicated in a number of disease conditions. These include endotoxemia and/or toxic shock syndrome {Tracey et al., *Nature* 330, 662–664 (1987) and Hinshaw et al., *Circ. Shock* 30, 279–292 (1990)}; cachexia {Dezube et al., *Lancet*, 335 (8690), 662 (1990)}; and Adult Respiratory Distress Syndrome where TNFα concentration in excess of 12,000 pg/milliliters have been detected in pulmonary aspirates from ARDS patients (Millar et al., *Lancet* 2 (8665), 712–714 (1989)). Systemic infusion of recombinant TNFα also resulted in changes typically seen in ARDS {Ferrai-Baliviera et al., *Arch. Surg.* 124(12), 1400–1405 (1989)}.

TNFα also appears to be involved in bone resorption diseases, including arthritis where it has been determined that when activated, leukocytes will produce a bone-resorbing activity, and data suggest that TNFα contributes to this activity {Bertolini et al., *Nature* 319, 516–518 (1986) and Johnson et al., *Endocrinology* 124(3), 1424–1427 (1989)}. It has been determined that TNFα stimulates bone resorption and inhibits bone formation in vitro and in vivo through stimulation of osteoclast formation and activation combined with inhibition of osteoblast function. Although TNFα may be involved in many bone resorption diseases, including arthritis, the most compelling link with disease is the association between production of TNFα by tumor or host tissues and malignancy associated hypercalcemia {*Calci. Tissue Int.* (US) 46 (Suppl.), S3–10 (1990)}. In Graft versus Host Disease, increased serum TNFα levels have been associated with major complications following acute allogenic bone marrow transplants {Holler et al., *Blood*, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of the disease and the prognosis in patients with acute malaria attacks {Grau et al., *N. Engl. J. Med.* 320 (24), 1586–1591 (1989)}.

TNFα also appears to play a role in the area of chronic pulmonary inflammatory diseases. The deposition of silica particles leads to silicosis, a disease of progressive respiratory failure caused by a fibrotic reaction. Antibodies to TNFα completely blocked the silica-induced lung fibrosis in mice {Pignet et al., *Nature*, 344:245–247 (1990)}. High levels of TNFα production (in the serum and in isolated macrophages) have been demonstrated in animal models of silica and asbestos induced fibrosis (Bissonnette et al., *Inflammation* 13(3), 329–339 (1989)). Alveolar macrophages from pulmonary sarcoidosis patients also have been found to release spontaneously massive quantities of TNFα, as compared with macrophages from normal donors {Baughman et al., *J. Lab. Clin. Med.* 115 (1), 36–42 (1990)}.

TNFα is also implicated in the inflammatory response which follows reperfusion (reperfusion injury) and is a major cause of tissue damage after loss of blood flow {Vedder et al., *PNAS* 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135 (1), 121–132 (1989)}.

Moreover, it is now known that TNFα is a potent activator of retrovirus replication including activation of HIV-1 {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1 and HIV-2, infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication in maintaining T lymphocyte activation. Therefore, interference with cytokine activity such as by prevention or inhibition of cytokine production, notably TNFα, in a HIV-infected individual aids in limiting the maintenance of T lymphocyte activation caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al., *Proc. Natl. Acad. Sci.*, 87, 782–784 (1990)}, therefore, prevention or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osborn, et al., *PNAS* 86, 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141 (1), 99–104 (1988)}.

TNFα has been implicated in other viral infections, such as the cytomegalia virus (CMV), influenza virus, adenovirus, and the herpes family of viruses for similar reasons as those noted.

It is recognized that suppression of the effects of TNFα can be beneficial in a variety of conditions and in the past, steroids such as dexamethasone and prednisolone as well as polyclonal and monoclonal antibodies {Beutler et al., *Science* 234, 470–474 (1985); WO 92/11383} have been employed for this purpose. Conditions in which inhibition of TNFα or NFκB is desirable include septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis and other arthritic conditions, Crohn's disease, ulcerative colitis, multiple sclerosis, systemic lupus erythrematosis, ENL in leprosy, radiation damage, and hyperoxic alveolar injury. The compounds can be used, under the supervision of qualified professionals, to inhibit the undesirable effects of TNFα, NFκB, or phosphodiesterase. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses or viral conjunctivitis, psoriasis, other skin disorders and diseases, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The compounds of this invention possess at least one center of chirality, that to which the depicted phenyl group is attached, and thus will exist as optical isomers. Both the racemates of these isomers and the individual isomers themselves, as well as diastereoisomers when there are two or more chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both isomers substantially free of the other; i.e., in a form having an optical purity of >95%.

Inhibition of production of TNFα by these compounds can be conveniently assayed using methods known in the art. For example, TNFα Inhibition Assays can be determined by a variety of known methods.

PBMC from normal donors is obtained by Ficoll-Hypaque density centrifugation. Cells are cultured in RPMI supplemented with 10% AB+ serum, 2 mM L-glutamine, 100 U/mL penicillin and 100 mg/mL streptomycin. The active compound is dissolved in DMSO (Sigma Chemical) and further dilutions are done in supplemented RPMI. The final DMSO concentration in the presence or absence of drug in the PBMC suspensions is 0.25 wt %. Test candidates are assayed at half-log dilutions starting at 50 mg/mL, being added to PBMC ($10^6$ cells/mL) in 96 wells plates one hour before the addition of LPS. PBMC ($10^6$ cells/mL) in the presence or absence of the compound is stimulated by treatment with 1 mg/mL of LPS from *Salmonella minnesota* R595 (List Biological Labs, Campbell, Calif.). Cells are then incubated at 37° C. for 18–20 hours. The supernatants then are harvested and assayed immediately for TNFα levels or frozen at −70° C. (for not more than 4 days) until assayed. The concentration of TNFα in the supernatant is determined by human TNFα ELISA kits (ENDOGEN, Boston, Mass.) according to the manufacturer's directions.

Particularly preferred are compounds in which $R^5$ is o-unsubstituted or substituted phenylene, $R^1$ is lower alkoxy, $R^3$ is monocycloalkyl of up to 10 carbon atoms, $R^6$ is —CO— or —CH$_2$—, Y is lower alkyl, —COZ or —C≡N, Z is —NH$_2$, —OH, or —O(lower alkyl), and n has a value of 0 or 1.

The compounds of the present invention can be prepared using methods known per se. For example, a cyclic acid anhydride or a lactone is allowed to react with the appropriate disubstituted phenyl compound:

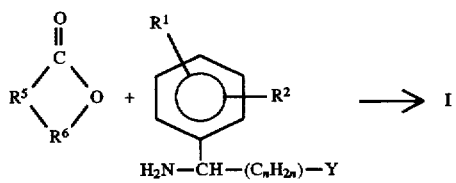

in which $R^1$, $R^2$, $R^5$, $R^6$, Y, and n are as defined above. The reaction can be effected simply by heating, analogously to the methods described in U.K. Patent Specification No. 1,036,694, the disclosure of which is incorporated herein by reference. Optionally acetic acid, with or without sodium acetate, can be added.

In place of the acid anhydride or lactone, one can utilize an N-carbethoxy derivative of the formula:

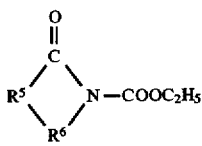

In a further embodiment, compounds in which $R^6$ is —$CH_2$— can be formed through condensation of a dialdehyde with a disubstituted phenyl compound in the presence of refluxing acetic acid utilizing the method of Griggs et al., *J. Chem. Soc., Chem. Comm.*, 1985, 1183–1184, the disclosure of which is incorporated herein by reference.

The disubstituted phenyl starting materials can be obtained through condensation of an appropriately substituted aldehyde and malonic acid, with intermediate formation of the phenyl amidine and subsequent decarboxylation.

The disubstituted aldehydes can be prepared utilizing classical methods for ether formation; e.g., reaction with the appropriate bromide in the presence of potassium carbonate. Numerous cycloalkyloxy benzaldehydes and procedures for preparing them are described in the literature. See, e.g., Ashton et al., *J. Med. Chem.*, 1994, 37, 1696–1703; Saccomano et al., *J. Med. Chem.*, 1994, 34, 291–298; and Cheng et al., *Org. and Med. Chem. Lett.*, 1995, 5(17), 1969–1972, the disclosures of which are incorporated herein by reference.

Representative starting materials include 3-cyclopentyloxy-4-methoxybenzaldehyde, 3-cyclopentyloxy-4-ethoxybenzaldehyde, 3-cyclohexyloxy-4-methoxybenzaldehyde, 3-(exo-bicyclo[2.2.1]hept-2-yloxy)-4-methoxybenzaldehyde, 3-(endo-bicyclo[2.2.1]hept-2-yl-oxy)-4-methoxybenzaldehyde, 3-(bicyclo[2.2.2]oct-2-yloxy)-4-methoxybenzaldehyde, 3-(bicyclo[3.2.1]oct-2-yloxy)-4-methoxybenzaldehyde, 3-indan-2-yloxy-4-methoxybenzaldehyde, and 3-(endo-benzo-bicyclo[2.2.1]hept-2-yloxy)-4-methoxybenzaldehyde.

The following examples will serve to further typify the nature of this invention but should not be construed as a limitation in the scope thereof, which scope is defined solely by the appended claims.

EXAMPLE 1

3-Amino-3-(3-cyclopentyloxy-4-methoxyphenyl) propionic Acid

A stirred suspension of 3-cyclopentyloxy-4-methoxybenzaldehyde (10.0 g, 45.4 mmol) and ammonium acetate (7.00 g, 90.8 mmol) in ethanol (95%, 30 mL) under nitrogen was heated to 45°–50° C. and malonic acid (4.72 g, 45.4 mmol) was added. The solution was heated at reflux for 24 hours. The mixture was allowed to cool to room temperature and was then filtered. The solid which is collected was washed with ethanol, air dried and then dried in vacuo (60° C., <1 mm) to afford 7.36 g (58%) of the product: mp 225°–226° C.; $^1$H NMR (D$_2$O/NaOH/TSP) δ 7.05–6.88 (m, 3H), 4.91–4.78 (m, 1H), 4.21–4.14 (m, 1H) 3.79 (s, 3H), 2.59–2.46 (m, 2H), 2.05–1.48 (m, 8H). Trace impurity peaks were present at 6.39 and 7.34 ppm. $^{13}$C NMR (D$_2$O/NaOD/TSP) δ 182.9, 150.7, 149.1, 140.6, 121.6, 116.0, 114.9, 83.9, 58.5, 55.3, 49.8, 34.9, 26.3.

Similarly prepared from 3-cyclopentyloxy-4-methoxybenzaldehyde, 3-cyclopentyloxy-4-ethoxybenzaldehyde, and 3-cyclohexyloxy-4-methoxybenzaldehyde are 3-amino-3-(3-cyclopentyloxy-4-methoxyphenyl)propionic acid, 3-amino-3-(3-cyclopentyloxy-4-ethoxyphenyl)propionic acid, and 3-amino-3-(3-cyclohexyloxy-4-methoxyphenyl)propionic acid, respectively.

EXAMPLE 2

3-Phthalimido-3-(3-cyclopentyloxy-4-methoxyphenyl)propionic Acid

To a stirred mixture of 3-amino-3-(3-cyclopentyloxy-4-methoxyphenyl)propionic acid (2.34 g, 8.40 mmol) and sodium carbonate (0.96 g, 9.05 mmol) in a mixture of water (20 mL) and acetonitrile (20 mL) under nitrogen was added N-carbethoxyphthalimide (1.9 g, 8.4 mmol). After 3 hours, the acetonitrile was removed in vacuo. The pH of the solution was adjusted to 1 with aqueous hydrogen chloride (4 N). Ether (5 mL) was added and the mixture stirred for 1 hour. The resulting slurry was filtered and the solid washed with water, air dried and then dried in vacuo (60° C., <1 mm) to afford 2.92 g (85%) of the product as a white solid: mp 159°–162° C.; $^1$H NMR (DMSO-$_6$) δ 12.40 (br s, 1H), 7.96–7.80 (m, 4H), 7.02 (s, 1H), 6.90 (s, 2H), 5.71–5.52 (m, 1H), 4.81–4.65 (m, 1H), 3.70 (s, 3H), 3.59–3.16 (m, 2H), 2.00–1.44 (m, 8H); $^{13}$C NMR (DMSO-d$_6$) δ 171.7, 167.6, 149.1, 146.8, 134.6, 131.2, 131.1, 123.1, 119.4, 113.9, 112.1, 79.5, 55.5, 50.1, 36.1, 32.1, 32.1, 23.5; Anal. Calcd for C$_{23}$H$_{23}$NO$_6$. Theoretical: C, 67.47; H, 5.66; N, 3.42. Found: C, 67.34; H, 5.59; N, 3.14.

Similarly prepared are 3-phthalimido-3-(3-cyclopentyloxy-4-methoxyphenyl)propionic acid, 3-phthalimido-3-(3-cyclopentyloxy- 4-ethoxyphenyl) propionic acid, 3-phthalimido-3-(3-cyclohexyloxy-4-methoxyphenyl)propionic acid, 3-phthalimido-3-{3-(bicyclo-[3.2.1]oct-2-yloxy)-4-methoxyphenyl}propionic acid, 3-phthalimido-3-{3-indan-2-yloxy-4-methoxyphenyl{propionic acid, and 3-phthalimido-3-{3-(endo-benzobicyclo[2.2.1]hept-2-yloxy)-4-methoxyphenyl}propionic acid.

EXAMPLE 3

3-Phthalimido-3-(3-cyclopentyloxy-4-methoxyphenyl)propionamide

A mixture of 3-phthalimido-3-(3-cyclopentyloxy-4-methoxyphenyl)propionic acid (2.05 g, 5.00 mmol), 1,1'-carbonyldiimidazole (0.91 g, 5.5 mmol) and 4-dimethylaminopyridine (trace) in tetrahydrofuran (20 mL) was stirred for 1.5 hours under nitrogen at approximately 25° C. To the solution was added ammonium hydroxide (1.07 mL, 16.0 mmol, 28–30%) and stirring was continued for 1.5 hours. A small amount of solid forms during this time. The mixture was concentrated to half its volume and a white solid precipitated. The mixture was filtered, washed with a small amount of tetrahydrofuran, air dried, and dried in vacuo (60° C.,<1 mm) to afford 1.27 g of the product. The product was further purified by flash column chromatography (silica gel, 5% methanol/methylene chloride) and the resulting white solid was dried in vacuo (60° C., <1 mm) to afford 1 g (49%) of the product: mp 165°–166° C.; $^1$H NMR (CDCl$_3$) δ 7.85–7.61 (m, 4H), 7.16–7.04 (m, 2H), 6.85–6.75 (m, 1H), 5.80 (dd, J=5.8, 10.4 Hz, 1H), 5.66 (br s, 1H), 5.54 (br s, 1H), 4.82–4.70 (m, 1H), 3.80 (s, 3H), 3.71 (dd, J=10.4, 15 Hz, 1H), 3.06 (dd, J=5.8, 15 Hz, 1H), 2.06–1.51 (m, 8H); $^{13}$C NMR (CDCl$_3$) δ 171.8, 168.3, 149.8, 147.7, 133.9, 131.8, 131.3, 123.3, 119.9, 114.6, 111.8, 80.4, 56.0, 51.6, 37.9, 32.7, 24.1; Anal. Calcd for C$_{23}$H$_{24}$N$_2$O$_5$. Theoretical: C, 67.63; H, 5.92; N, 6.86. Found: C, 67.25; H, 5.76; N, 6.68.

Similarly prepared are 3-phthalimido-3-(3-cyclopentyloxy-4-methoxyphenyl)propionamide, 3-phthalimido-3-(3-cyclopentyloxy-4-ethoxyphenyl) propionamide, 3-phthalimido-3-(3-cyclohexyloxy-4-methoxyphenyl)propionamide, 3-phthalimido-3-(3-(endo-bicyclo-[2.2.1]hept-2-yloxy)-4-methoxyphenyl}propionamide, 3-phthalimido-3-{3-(bicyclo[2.2.2]oct-2-yloxy)-4-methoxyphenyl}propionamide, 3-phthalimido-3-{3-(bicyclo[3.2.1]oct-2-yloxy)-4-methoxyphenyl}-propionamide, 3-phthalimido-3-{3-indan-2-yloxy-4-methoxyphenyl-{propionamide, and 3-phthalimido-3-{3-(endo-benzobicyclo[2.2.1]-hept-2-yloxy)-4-methoxyphenyl}propionamide.

EXAMPLE 4

Methyl 3-amino-3-(3-cyclopentyloxy-4-methoxyphenyl)propionate

To a cooled (ice bath temperature) and stirred mixture of 3-amino-3-(3-cyclopentyloxy-4-methoxyphenyl)propionic acid (3.00 g, 10.7 mmol) in methanol (20 mL) under nitrogen was added thionyl chloride (1.8 mL, 2.3 mmol) dropwise via syringe. The resulting solution was stirred at 0° C. for 1 hour, the ice bath was removed and stirring was continued at RT for 1 hour and a white solid precipitated. The methanol was removed and the solid was slurried in hexane. The mixture was filtered and the white solid was washed with hexane, air dried and then dried in vacuo (60° C., <1 mm) to afford 2.69 g (76%) of the product as the hydrochloride salt: mp 183°–184.5° C.; $^1$NMR (DMSO-$d_6$) δ 8.76 (br s, 3H), 7.25 (s, 1H), 7.06–6.89 (m, 2H), 4.85–4.75 (m, 1H), 4.58–4.44 (m, 1H), 3.74 (s, 3H), 3.55 (s, 3H), 3.31–2.86 (m, 2H), 2.06–1.44 (m, 8H); $^{13}$C NMR (DMSO-$d_6$) δ 169.1, 149.3, 146.5, 128.4, 119.5, 113.5, 111.4, 79.0, 55.0, 51.2, 50.3, 38.2, 31.7, 31.6, 23.0; Anal. Calcd for $C_{16}H_{24}ClNO_4$. Theoretical.: C, 58.27; H, 7.33; N, 4.25. Found: C, 58.44; H, 7.34; N, 4.13.

Similarly prepared are methyl 3-amino-3-(3-cyclopentyloxy-4-methoxyphenyl)propionate, methyl 3-amino-3-(3-cyclopentyloxy-4-ethoxyphenyl)propionate, and methyl 3-amino-3-(3-cyclohexyloxy-4-methoxyphenyl)propionate, all as the hydrochloride.

EXAMPLE 5

Methyl 3-phthalimido-3-(3cyclopentyloxy-4-methoxyphenyl)propionate

To a stirred solution of methyl 3-amino-3-(3-cyclopentyloxy-4-methoxyphenyl)propionate hydrochloride (0.50 g, 1.52 mmol) and sodium carbonate (0.16 g, 1.52 mmol) in a mixture of water (5 mL) and acetonitrile (5 mL) under nitrogen was added N-carbethoxyphthalimide (0.34 g, 1.52 mmol). The solution was stirred for 3 hours at RT. The acetonitrile was removed in vacuo which afforded a two layer mixture which was extracted with methylene chloride (3×15 mL). The combined organic extracts were dried over magnesium sulfate, filtered and then Concentrated in vacuo to afford 0.77 g of the crude product as an oil. The crude product was purified by flash column chromatography (silica gel, 35/65, ethyl acetate/hexane) the resulting glassy solid was dried in vacuo to afford 0.48 g (75%) of the product as a white solid: mp 76°–78° C.; $^1$H NMR (CDCl$_3$) δ 7.86–7.60 (m, 4H), 7.19–7.00 (m, 2H), 6.88–6.72 (m, 1H), 5.84–5.67 (m, 1H), 4.85–4.70 (m, 1H), 3.80 (s, 3H), 3.80–3.69 (m, 1H), 3.63 (s, 3H), 3.34–3.15 (m, 1H), 2.10–1.48 (m, 8H); $^{13}$C NMR (CDCl$_3$) δ 171.0, 168.0, 149.8, 147.6, 133.9, 131.8, 130.9, 123.2, 120.1, 114.6, 111.7, 80.4, 55.9, 51.8, 50.7, 35.9, 32.7, 24.0; Anal. Calcd for $C_{24}H_{25}NO_6$. Theoretical: C, 68.03; H, 5.95; N, 3.31. Found: C, 67.77; H, 5.97; N, 3.20.

Similarly prepared are methyl 3-phthalimido-3-(3-cyclopentyloxy-4-methoxyphenyl)propionate, methyl 3-phthalimido-3-(3-cyclopentyloxy-4-ethoxyphenyl) propionate, and methyl 3-phthalimido-3-(3-cyclohexyloxy-4-methoxyphenyl)propionate.

EXAMPLE 6

3-Amino-3-(3-{exo-bicyclo[2.2.1]hept-2-yloxy}-4-methoxyphenyl)propionic Acid A stirred suspension of 3-(exo-bicyclo[2.2.1]hept-2-yloxy)-4-methoxybenzaldehyde (6.00 g, 24.4 mmol) and ammonium acetate (3.76 g, 48.8 mmol) in ethanol (95%, 20 mL) under nitrogen was heated to 45°–50° C. and malonic acid (2.53 g, 24.4 mmol) was added. The solution was refluxed for 24 hours, allowed to cool to room temperature, and filtered. The solid was washed with ethanol, air dried, and dried in vacuo (60° C., <1 mm) to afford 3.17 g (43%) of the product: mp 225°–226° C.; $^1$H NMR (D$_2$O/NaOD/TSP) δ 7.09–6.90 (m, 3H), 4.41–4.28 (m, 1H), 4.27–4.15 (m, 1H), 3.82 (s, 3H), 2.64–2.48 (m, 2H) 2.44 (s, 1H), 2.31 (s, 1H), 1.92–1.76 (m, 1H), 1.69–1.38 (m, 4H), 1.30–1.05 (m, 3H).

Similarly prepared from 3-(endo-bicyclo[2.2.1]hept-2-yloxy)-4-methoxybenzaldehyde, 3-(bicyclo[2.2.2]oct-2-yloxy)-4-methoxybenzaldehyde, 3-(bicyclo[3.2.1]oct-2-yloxy)-4-methoxybenzaldehyde, 3-indan-2-yloxy-4-methoxybenzaldehyde, and 3-(endo-benzobicyclo[2.2.1] hept-2-yloxy)-4-methoxybenzaldehyde are 3-amino-3-(3-(endo-bicyclo[2.2.1]hept-2-yloxy)-4-methoxyphenyl}propionic acid, 3-amino-3-{3-(bicyclo[2.2.2]oct-2-yloxy)-4-methoxyphenyl}propionic acid, 3-amino-3-{3-(bicyclo[3.2.1]oct-2-yloxy)-4-methoxyphenyl}propionic acid, 3-amino-3-{3-indan-2-yloxy-4-methoxyphenyl{propionic acid, and 3-amino-3-{3-(endo-benzobicyclo[2.2.1]hept-2-yloxy)-4-methoxyphenyl}propionic acid, respectively.

EXAMPLE 7

Methyl 3-Amino-3-(3-{exo-bicyclo[2.2.1]hept-2-yloxy}-4-methoxyphenyl)propionate Hydrochloride To an ice bath cooled stirred suspension of 3-amino-3-(3-{exo-bicyclo[2.2.1]hept-2-yloxy}-4-methoxyphenyl) propionic acid (2.00 g, 6.55 mmol) in methanol (15 mL) under nitrogen was added thionyl chloride (1.56 mL, 13.1 mmol) dropwise via syringe. The resulting solution was stirred at 0° C. for 30 minutes, the ice bath was removed and stirring was continued at room temperature for 2.5 hours. The methanol was removed and the solid slurried in hexane (15 mL). The mixture was filtered and the white solid washed with hexane, air dried and then dried in vacuo (60° C., <1 mm) to afford 1.97 g (85%) of the product: mp 197.5°–201.5° C.; $^1$H NMR (DMSO-$d_6$) δ 7.50 (br s, 3H), 7.18 (s, 1H), 7.07–6.88 (m, 2H), 4.56–4.42 (m, 1H), 4.30–4.19 (m, 1H), 3.74 (s, 3H), 3.54 (s, 3H), 3.41–2.85 (m, 3H), 2.37 (s, 1H), 2.27 (s, 1H), 1.92–1.75 (m, 1H), 1.64–1.03 (m, 6H); $^{13}$C NMR (DMSO-$d_6$) δ 169.4, 149.6, 146.4, 128.8, 120.0, 119.9, 113.8, 111.8, 80.1, 79.9, 55.5, 51.6, 50.7, 40.5, 39.2, 38.6, 34.8, 27.8, 23.7, 23.6.

Similarly prepared are methyl 3-amino-3-(3-(endo-bicyclo-[2.2.1]hept-2-yloxy)-4-methoxyphenyl}propionate, methyl 3-amino-3-(3-(bicyclo[2.2.2]oct-2-yloxy)-4-methoxyphenyl}propionate, methyl 3-amino-3-(3-(bicyclo[3.2.1]oct-2-yloxy)-4-methoxyphenyl)-propionate, methyl 3-amino-3-(3-indan-2-yloxy-4-methoxyphenyl-{propionate, and methyl 3-amino-3-{3-(endo-benzobicyclo[2.2.1]hept-2-yloxy)-4-methoxyphenyl)propionate.

EXAMPLE 8

By following the procedure of Example 3 but substituting 3-phthalimido-3-(3-{exo-bicyclo[2.2.1]hept-2-yloxy}-4-methoxyphenyl)propionic acid, there is obtained 3-phthalimido-3-(3-{exo-bicyclo[2.2.1]hept-2-yloxy}-4-methoxyphenyl)propionamide.

Similarly prepared are 3-phthalimido-3-{3-(endo-bicyclo-[2.2.1]hept-2-yloxy)-4-methoxyphenyl}propionamide, 3-phthalimido-3-{3-(bicyclo[2.2.2]oct-2-yloxy)-4-methoxyphenyl}propionamide, 3-phthalimido-3-{3-(bicyclo[3.2.1]oct-2-yloxy)-4-methoxyphenyl}-propionamide, 3-phthalimido-3-{3-indan-2-yloxy-4-methoxyphenyl-{propionamide, and 3-phthalimido-3-{3-(endo-benzobicyclo[2.2.1]-hept-2-yloxy)-4-methoxyphenyl}propionamide.

EXAMPLE 9

Methyl 3-Phthalimido-3-(3-{exo-bicyclo[2.2.1]hept-2-yloxy}-4-methoxyphenyl)propionate To a stirred solution of methyl 3-amino-3-(3-{exo-bicyclo-[2.2.1]hept-2-yloxy}-4-methoxyphenyl)propionate hydrochloride (1.00 g, 2.81 mmol) and sodium carbonate (0.3 g, 2.8 mmol) in a mixture of water (10 mL) and acetonitrile (10 mL) under nitrogen was added N-carbethoxyphthalimide (0.64 g, 2.81 mmol). The solution was stirred for 3 hours at room temperature. The acetonitrile was remove in vacuo and the residue extracted with methylene chloride (3×30 ml). The combined organic extracts were dried over magnesium sulfate, filtered and concentrated in vacuo to afford 1.44 g of the product. The product was further purified by flash column chromatography (silica gel, 20%, ethyl acetate/methylene chloride) to afford a white solid which was then dried in vacuo to afford 0.23 g (18%) of product: mp 47°–48° C.; $^1$H NMR (CDCl$_3$) δ 7.86–7.61 (m, 4H), 7.14–7.00 ( m, 2H), 6.82–6.74 (m, 1H), 5.75 (dd, J=5.9, 10 Hz, 1H), 4.25–4.14 (m, 1H), 3.84–3.69 (m, 1H), 3.79 (s, 3H), 3.63 (s, 3H), 3.23 (dd, J=5.9, 16.5 Hz, 1H), 2.51–2.41 (m, 1H), 2.34–2.24 (m, 1H), 1.86–1.06 (m, 8H); $^{13}$C NMR (CDCl$_3$) δ 171.1, 168.1, 149.7, 147.2, 133.9, 131.8, 130.9, 123.3, 120.1, 120.0, 114.5, 114.4, 111.8, 81.1, 56.0, 51.9, 50.8, 41.1, 41.0, 39.9, 39.8, 35.9, 35.5, 35.3, 28.4, 24.3; HPLC 97%; Anal. Calcd for $C_{26}H_{27}NO_6$. Theoretical: C, 69.47; H, 6.05; N, 3.12. Found: C, 69.22; H, 5.91; N, 2.95.

Similarly prepared are methyl 3-phthalimido-3-{3-(endo-bicyclo[2.2.1]hept-2-yloxy)-4-methoxyphenyl}propionate, methyl 3-phthalimido-3-{3-(bicyclo[2.2.2]oct-2-yloxy)-4-methoxyphenyl}propionate, methyl 3-phthalimido-3-{3-(bicyclo[3.2.1]oct-2-yloxy)-4-methoxyphenyl}propionate, methyl 3-phthalimido-3-{3-indan-2-yloxy-4-methoxyphenyl{propionate, and methyl 3-phthalimido-3-{3-(endo-benzobicyclo[2.2.1]hept-2-yloxy)-4-methoxyphenyl}propionate.

EXAMPLE 10

1-(3-Cyclopentoxy-4-methoxyphenyl)propylamine

To an ice bath cooled stirred solution of 1,1,1,3,3,3-hexamethyldisilazane (2.5M, 4.1 mL, 19.5 mmol) in tetrahydrofuran (5 mL) under nitrogen, was added a hexane solution of butyl lithium (7.2 mL, 18 mmol) via syringe. The ice bath was removed and the solution was stirred for 30 minutes at room temperature. This solution then was added dropwise to an ice bath cooled solution of 3-cyclopentoxy-4-methoxybenzaldehyde (3.3 g, 15 mmol) in tetrahydrofuran (5 mL) and the mixture stirred for 20 minutes. An ethereal solution of ethylmagnesium bromide (3M, 10 mL, 30 mmol) then was added dropwise. The reaction solution was allowed to reach room temperature and then was stirred at room temperature. The reaction progress was monitored by HPLC (Waters Nova-Pak/EC 18 column, 3.9×150 mm, 4 micron, 1 mL/min, 240 nm, 35/65, CH$_3$CN/0.1% H$_3$PO$_4$ (aq)) and after 3 hours no starting material remained. The reaction mixture was slowly poured into a saturated solution of ammonium chloride (100 mL). The resulting mixture was extracted with methylene chloride (3×20 mL) and the combined extracts were dried over magnesium sulfate and concentrated in vacuo to yield 5.6 g of product which was further purified by flash column chromatography (silica gel, 250/10/1, methylene chloride/methanol/ammonium hydroxide) to afford 2.5 g (67%) of the product as an oil: 1H NMR (CDCl$_3$) δ 6.91–6.77 (m, 3H), 4.85–4.74 (m, 1H), 3.83 (s, 3H), 3.74 (t, J=6.8 Hz, 1H), 2.02–1.15 (m, 12H), 0.86 (t, J=7.4 Hz, 3H); $^{13}$C NMR (CDCl$_3$) δ 148.8, 147.5, 138.8, 118.4, 113.3, 111.8, 80.3, 57.4, 56.0, 32.7, 32.4, 10.9.

EXAMPLE 11

3-Phthalimido-3-(3-cyclopentoxy-4-methoxyphenyl) propane

To a stirred solution of 1-(3-cyclopentoxy-4-methoxyphenyl)propylamine (1 g, 4 mmol) and sodium carbonate (0.42 g, 4.0 mmol) in a mixture of water (5 mL) and acetonitrile (5 mL) under nitrogen was added N-carbethoxyphthalimide (0.9 g, 4.0 mmol). The solution was stirred for 2.5 hours at room temperature. The acetonitrile was remove in vacuo which resulted in the precipitation of a white solid. The mixture was filtered and the solid was washed with water, air dried and then dried in vacuo to afford 1.25 g (83%) of product: mp 100.0°–102.5° C.; 1H NMR (CDCl$_3$) δ 7.87–7.61 (m, 4H), 7.21–7.01 (m, 2H), 6.85–6.75 (m, 1H), 5.15 (dd, J=7, 9.3 Hz, 1H), 4.86–4.74 (m, 1H), 3.81 (s, 3H), 2.66–2.20 (m, 2H), 2.08–1.47 (m, 8H), 0.95 (t, J=7.3 Hz, 3H); $^{13}$C NMR (CDCl$_3$) δ 168.4, 149.4, 147.5, 133.8, 132.2, 131.9, 123.1, 120.5, 115.0, 111.5, 80.3, 55.6, 55.9, 32.7, 24.4, 11.6; HPLC (Waters Nova-Pak/EC 18 column, 3.9×150 mm, 4 micron, 1 mL/min, 240 nm, 60/40. CH$_3$CN/0.1% H$_3$PO$_4$(aq)) 12 min, 99%; Anal. Calcd for $C_{23}H_{25}NO_4$. Theoretical: C, 72.80; H, 6.64; N, 3.69. Found: C, 72.72; H, 6.69; N, 3.65.

EXAMPLE 12

1-(3-Indanyloxy-4-methoxyphenyl)propylamine

To an ice bath cooled stirred solution of 1,1,1,3,3,3-hexamethyldisilazane (2.7 mL, 13 mmol) in tetrahydrofuran (5 mL) under nitrogen, was added a hexane solution of butyl lithium (2.5M, 4.8 mL, 12 mmol) via syringe. The ice bath was removed and the solution was stirred for 25 minutes at room temperature. This solution then was added dropwise to an ice bath cooled solution of 3-indanyloxy-4-methoxybenzaldehyde (2.68 g, 10.0 mmol) in tetrahydrofuran (4 mL) and the mixture was stirred for one hour. An ethereal solution of ethylmagnesium bromide (3M, 6.7 mL, 20 mmol) then was added dropwise via syringe. The reaction mixture was heated at reflux and was monitored by HPLC (Waters Nova-Pak/EC 18 column, 3.9×150 mm, 4 micron, 1 mL/min, 240 nm, 40/60, $CH_3CN$/0.1% $H_3PO_4$(aq)). After 48 hours the reaction had reached completion and was allowed to cool to room temperature. The reaction mixture then was slowly poured into a saturated solution of ammonium chloride (80 mL). The resulting mixture was extracted with methylene chloride (3×15 mL) and the combined extracts were dried over magnesium sulfate and concentrated to afford the product which was further purified by flash column chromatography (silica gel, 250/10/1, methylene chloride/methanol/ammonium hydroxide) to afford 0.27 g (9%) of product as an orange solid.

EXAMPLE 13

1-Phthalimido-1-(3-indanyloxy-4-methoxyphenyl) propane

To a stirred solution of 1-(3-indanyloxy-4-methoxyphenyl)propylamine (0.25 g, 0.84 mmol) and sodium carbonate (0.09 g, 0.84 mmol) in a mixture of water (2 mL) and acetonitrile (2 mL) under nitrogen was added N-carbethoxyphthalimide (0.19 g, 0.84 mmol). The solution was stirred for 4 hours at room temperature. The acetonitrile was removed in vacuo and the resulting mixture was extracted with methylene chloride (2×10 mL), dried over magnesium sulfate and concentrated in vacuo to afford 0.35 g of the product which was further purified by flash column chromatography (silica gel, 25/75, ethyl acetate/hexane) to afford 0.19 g (48%) of the product as a solid: mp 62° C.; $^1$H NMR ($CDCl_3$) δ 7.86–7.63 (m, 4H), 7.29–7.04 (m, 6H), 6.87–6.78 (m, 1H), 5.30–5.14 (m, 2H), 3.77 (s, 3H), 3.52–3.14 (m, 4H), 2.66–2.21 (m, 2H), 0.97 (t, J=7.3 Hz, 3H); $^{13}$C NMR ($CDCl_3$) δ 168.4, 149.6, 147.1, 140.7, 140.6, 133.8, 132.2, 131.8, 126.5, 124.6, 123.1, 121.2, 115.3, 111.7, 79.0, 56.5, 55.9, 39.6, 39.6, 24.4, 11.6; HPLC (Waters Nova-Pak/EC 18 column, 3.9×150 mm, 4 micron, 1 mL/min, 240 nm, 60/40, $CH_3CN$/0.1% $H_3PO_4$ (aq)) 12 min, 98%; Anal. Calcd for $C_{27}H_{25}NO_4$. Theoretical: C, 75.86; H, 5.89; N, 3.28. Found: C, 75.58; H, 5.90; N, 3.20.

EXAMPLE 14

1-(1-Oxoisoindoline)-1-(3-cyclopentoxy-4-methoxyphenyl)propane

A stirred solution of phthalic dicarboxaldehyde (0.4 g, 3 mmol) and 1-(3-cyclopentoxy-4-methoxyphenyl) propylamine (0.75 g, 3.0 mmol) in glacial acetic acid (9 mL) under nitrogen was heated at reflux for 5 minutes. The stirred reaction then was allowed to cool to room temperature and concentrated in vacuo to afford the product which was further purified by flash column chromatography on silica gel, first with 40/60 ethyl acetate/hexane and then with 15/85, ethyl acetate/methylene chloride) to afford 0.48 g (44%) of the product as a yellow oil: 1H NMR ($CDCl_3$) δ 7.97–7.76 (m, 1H), 7.61–7.31 (m, 3H), 7.06–6.74 (m, 3H), 5.54–5.39 (m, 1H), 4.87–4.66 (m, 1H), 4.28 (d, J=17 Hz, 1H), 4.00 (d, J=17 Hz, 1H), 3.82 (s, 3H), 2.25–1.45 (m, 10H), 0.99 (t, J=7.3 Hz, 3H); $^{13}$C NMR ($CDCl_3$) δ 168.3, 149.4, 147.5, 141.1, 132.7, 132.2, 130.9, 127.7, 123.5, 122.6, 119.3, 114.9, 111.6, 80.3, 55.9, 55.8, 45.3, 32.6, 32.5, 24.2, 23.8, 10.9; HPLC (Waters Nova-Pak/EC 18 column, 3.9×150 mm, 4 micron, 1 mL/min, 240 nm, 50/50, $CH_3CN$/ 0.1% $H_3PO_4$) 8 min, 100%.

EXAMPLE 15

3-(1-Oxoisoindoline)-3-(3-cyclopentyloxy-4-methoxyphenyl)-propionic Acid

A stirred solution of phthalic dicarboxaldehyde (0.67 g, 5.00 mmol) and 3-amino-3-(3-cyclopentyloxy-4-methoxyphenyl)propanoic acid (1.40 g, 5.01 mmol) in 20 mL of glacial acetic acid under nitrogen was heated to reflux for 5 minutes. The stirred reaction then was allowed to cool to room temperature overnight. The resulting yellow brown solution was concentrated in vacuo and the solid which formed slurried in ethyl acetate (25 mL). The slurry was filtered and the solid dried in vacuo to afford 1.52 g (77%) of the product as a white powder: mp 161°–163° C.; $^1$H NMR (dmso-$D_6$/TMS) δ 12.33 (br s, 1 H, COOH), 7.75–7.4 (m , 4 H, Ar), 7.05–6.8 (m, 3 H, Ar), 5.66 (app. t, J=7.9 Hz, 1 H), 4.75 (m, 1 H), 4.51 (d, J=17.7 Hz, 1 H), 4.11 (d, J=17.7 Hz, 1 H), 3.71 (s, 3 H), 3.12 (m, 2 H), 1.95–1.45 (m, 8 H); $^{13}$C NMR (dmso-$D_6$/TMS) δ 171.8, 149.1, 146.8, 141.6, 132.1, 131.5, 131.3, 127.8, 123.4, 122.8, 119.2, 114.0, 112.2, 79.4, 55.5, 51.0, 46.3, 36.7, 32.1, 32.0, 23.4. Anal. Calcd for $C_{23}H_{25}NO_5$. Theory: C, 69.86; H, 6.37; N, 3.54. Found: C, 69.59; H, 6.35; N, 3.44.

EXAMPLE 16

Methyl 3-(1-oxoisoindoline)-3-(3-cyclopentyloxy-4-methoxyphenyl)propionate.

To a stirred suspension of 3-(1-oxoisoindoline)-3-(3-cyclopentyloxy-4-methoxyphenyl)propionic acid (0.758 g, 1.92 mmol) in 10 mL of methanol cooled in an ice bath and under nitrogen was added 0.3 mL of thionyl chloride. After stirring for 15 minutes, the mixture was allowed to warm to room temperature and stirred overnight. The solvent was evaporated and the residue dissolved in methylene chloride and washed with saturated aqueous sodium bicarbonate solution and brine. The organic layer was dried over sodium sulfate and concentrated in vacuo. The residue was purified by flash chromatography (silica gel, 1/9 ethyl acetate/ methylene chloride) to afford 0.6 g of the product which was stirred in hexane. The slurry was filtered to afford 0.32 g of the product as a white solid: mp 94.5°–95.5° C.; $^1$H NMR ($CDCl_3$/TMS) δ 7.85 (d , J=6.7 Hz, 1 H, Ar), 7.55–7.3 (m, 3 H, Ar), 7.0–6.75 (m, 3 H), 5.92 (dd, J=9.1, 7.0 Hz, 1 H), 4.74 (m, 1 H), 4.37 (d, J=16.7 Hz, 1 H), 4.07 (d, J=16.7 Hz, 1 H), 3.82 (s, 3 H), 3.64 (s, 3 H), 3.23 (dd, J=9.1, 15.0 Hz, 1 H), 3.10 (dd, J=9.1, 15.0 Hz, 1 H), 2.05–1.45 (m, 8 H); $^{13}$C NMR ($CDCl_3$/TMS) δ 170.9, 149.8, 147.8, 141.3, 132.6, 131.3, 131.0, 127.9, 123.8, 122.7, 119.0, 114.6, 111.8, 80.5, 56.0, 52.0, 51.7, 46.6, 40.0, 32.7, 32.7, 24.0. Anal. Calcd for $C_{24}H_{27}NO_5$. Theory: C, 70.40; H, 6.65; N, 3.42. Found: C, 70.07; H, 6.63; N, 3.34.

EXAMPLE 17

Tablets, each containing 50 milligrams of active ingredient, can be prepared in the following manner:

| Constituents (for 1000 tablets) | |
| --- | --- |
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 18

Tablets, each containing 100 milligrams of active ingredient, can be prepared in the following manner:

| Constituents (for 1000 tablets) | |
|---|---|
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 19

Tablets for chewing, each containing 75 milligrams of active ingredient, can be prepared in the following manner:

| Composition (for 1000 tablets) | |
|---|---|
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 20

Tablets, each containing 10 milligrams of active ingredient, can be prepared in the following manner:

| Composition (for 1000 tablets) | |
|---|---|
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 21

Gelatin dry-filled capsules, each containing 100 milligrams of active ingredient, can be prepared in the following manner:

| Composition (for 1000 capsules) | |
|---|---|
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 22

A 0.2% injection or infusion solution can be prepared, for example, in the following manner:

| | |
|---|---|
| active ingredient | 5.0 grams |
| sodium chloride | 22.5 grams |
| phosphate buffer pH 7.4 | 300.0 grams |
| demineralized water | to 2500.0 mL |

The active ingredient is dissolved in 1000 milliliters of water and filtered through a microfilter or slurried in 1000 mL of $H_2O$. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:
1. A compound of the formula:

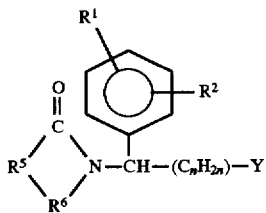

in which:
one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl, bicycloalkyl, benzocycloalkyl of up to 18 carbon atoms;

X is a carbon-carbon bond, —$CH_2$—, or —O—;

$R^5$ is o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, aminoalkyl, or lower alkoxy;

$R^6$ is —CO—, —$CH_2$—, or —$CH_2CO$—;

Y is —COZ, —C≡N, —$OR^8$, lower alkyl, or aryl;

Z is —$NH_2$, —OH, —NHR, —$R^9$, or —$OR^9$;

$R^8$ is hydrogen or lower alkyl;

$R^9$ is lower alkyl or benzyl; and, n has a value of 0, 1, 2, or 3.

2. A compound according to claim 1 wherein one of $R^1$ and $R^2$ is $R^3$—O— and the other is lower alkyl, lower alkoxy, or $R^3$—O—;

$R^3$ is cyclic or bicyclic alkyl of up to 10 carbon atoms;

$R^5$ is o-phenylene, unsubstituted or substituted with 1 to 3 substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms;

$R^6$ is —CO— or —$CH_2$—;

Y is —COZ or lower alkyl;

Z is —$NH_2$, —OH, —NHR, —$R^9$, or —$OR^9$;

$R^9$ is alkyl or benzyl; and n has a value of 1 or 2.

3. A compound according to claim 1 wherein $R^5$ is o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, or lower alkoxy;

$R^1$ is lower alkoxy;

$R^3$ is monocycloalkyl of up to 10 carbon atoms;

$R^6$ is —CO—;

Y is —COZ or —C≡N;

Z is —$NH_2$, —OH, or —O(lower alkyl); and n has a value of 0 1.

4. A compound selected from the group consisting of 3-phthalimido-3-(3-cyclopentyloxy-4-methoxyphenyl) propionic acid, 3-phthalimido-3-(3-cyclopentyloxy-4-methoxyphenyl)propionamide, methyl 3-phthalimido-3-(3-cyclopentyloxy-4-methoxyphenyl)propionate, methyl 3-phthalimido-3-(3-{exo-bicyclo[2.2.1]hept-2-yloxy}-4-methoxyphenyl)propionate, methyl 3-phthalimido-3-(3-cyclopentyloxy-4-methoxyphenyl)propionate, 3-phthalimido-3-(3-cyclopentyloxy-4-hydroxyphenyl) propionic acid, 3-phthalimido-3-(3-cyclohexyloxy-4-methoxyphenyl)propionic acid, 3-phthalimido-3-{3-(bicyclo[3.2.1]oct-2-yloxy)-4-methoxyphenyl}propionic acid, 3-phthalimido-3-{3-indan-2-yloxy-4-methoxyphenyl{propionic acid, 3-phthalimido-3-{3-(endo-benzobicyclo[2.2.1]hept-2-yloxy)-4-methoxyphenyl}propionic acid, 3-phthalimido-3-(3-cyclopentyloxy-4-hydroxyphenyl)propionamide, 3-phthalimido-3-(3-cyclohexyloxy-4-methoxyphenyl) propionamide, 3-phthalimido-3-{3-(endo-bicyclo[2.2.1] hept-2-yloxy)-4-methoxyphenyl}propionamide, 3-phthalimido-3-{3-(bicyclo[2.2.2]oct-2-yloxy)-4-methoxyphenyl}propionamide, 3-phthalimido-3-}3-(bicyclo-[3.2.1]oct-2-yloxy)-4-methoxyphenyl}propionamide, 3-phthalimido-3-{3-indan-2-yloxy-4-methoxyphenyl{propionamide, and 3-phthalimido-3-}3-(endo-benzobicyclo[2.2.1]hept-2-yloxy)-4-methoxyphenyl}propionamide.

* * * * *